United States Patent
Peng et al.

(10) Patent No.: US 10,499,877 B2
(45) Date of Patent: Dec. 10, 2019

(54) MECHANICALLY ROTATING INTRAVASCULAR ULTRASOUND PROBE

(71) Applicant: Shenzhen University, Guangdong (CN)

(72) Inventors: Jue Peng, Guangdong (CN); Siping Chen, Guangdong (CN); Tianfu Wang, Guangdong (CN)

(73) Assignee: SHENZHEN UNIVERSITY, Shenzhen, Guangdong (CN)

( * ) Notice: Subject to any disclaimer, the term of this patent is extended or adjusted under 35 U.S.C. 154(b) by 1079 days.

(21) Appl. No.: 14/689,785

(22) Filed: Apr. 17, 2015

(65) Prior Publication Data
US 2015/0297182 A1  Oct. 22, 2015

(30) Foreign Application Priority Data
Apr. 17, 2014  (CN) .......................... 2014 1 0153476

(51) Int. Cl.
*A61B 8/00*  (2006.01)
*G01S 15/89*  (2006.01)
*A61B 8/12*  (2006.01)

(52) U.S. Cl.
CPC .............. *A61B 8/4461* (2013.01); *A61B 8/12* (2013.01); *A61B 8/4281* (2013.01); *A61B 8/445* (2013.01);
(Continued)

(58) Field of Classification Search
CPC ........... A61B 8/0891; A61B 8/12; A61B 8/14; A61B 18/1492; A61B 18/445;
(Continued)

(56) References Cited

U.S. PATENT DOCUMENTS 7,488,289 B2 * 2/2009 Suorsa ................. A61B 8/0841
                                                  600/445
2002/0158546 A1 * 10/2002 Nakatani ............. H02N 11/006
                                                  310/300
(Continued)

FOREIGN PATENT DOCUMENTS

EP  2114004  11/2009

OTHER PUBLICATIONS

Liu, Tingyi et al. "Electrostatic Side-Drive Rotary Stage on Liquid-Ring Bearing," Journal of Mircoelectromechanical Systems: vol. 23, No. 1, pp. 147-156; Feb. 2014.*
(Continued)

*Primary Examiner* — Thomas J Hong
*Assistant Examiner* — Helene Bor
(74) *Attorney, Agent, or Firm* — Hamre, Schumann, Mueller & Larson, P.C.

(57) ABSTRACT

A mechanically rotating intravascular ultrasound probe relates to the technical field of medical devices, and aims to provide a forward-looking mechanically rotating intravascular ultrasound probe having a small volume, a high image resolution and good imaging stability. The intravascular ultrasound probe includes a catheter, an ultrasonic transducer disposed at a front end of a cavity of the catheter and a driving apparatus that drives the ultrasonic transducer to rotate mechanically. The driving apparatus is a micro motor disposed in the cavity of the catheter, including a rotor and a stator. The ultrasonic transducer is installed on top of the rotor and electrically connected to the rotor, and the rotor is also electrically connected to the stator; the catheter is a magnetic metal tube, and a front end thereof is enclosed by an acoustic window which has a spherical tip and allows ultrasonic waves of the ultrasonic transducer to pass through; the acoustic window is filled with an ionic liquid (Continued)

having a function of a ultrasonic coupling agent. The ultrasound probe solves a problem of rotation torsion of an image when the catheter passes through a lesion with high-grade stenosis or a curved blood vessel section, and achieves forward scanning imaging and side scanning imaging for a blood vessel wall.

12 Claims, 1 Drawing Sheet

(52) U.S. Cl.
CPC .............. *A61B 8/56* (2013.01); *G01S 15/894* (2013.01); *A61B 8/4494* (2013.01)

(58) Field of Classification Search
CPC ........... A61B 2018/00011; A61B 2018/00357; A61B 2018/00404; A61B 2018/00434; A61B 2018/00511; A61B 2018/00577; A61B 2018/00839; A61B 8/4494; A61B 8/4281; A61B 8/445; A61B 8/56; G01S 15/84; G01S 15/894
See application file for complete search history.

(56) References Cited

U.S. PATENT DOCUMENTS

| 2005/0027198 | A1 | 2/2005 | Couvillon |
| 2005/0113685 | A1 | 5/2005 | Maschke et al. |
| 2007/0278914 | A1* | 12/2007 | Verfaillie ............... A47B 61/00 312/226 |
| 2010/0168570 | A1* | 7/2010 | Sliwa ...................... A61B 8/12 600/439 |
| 2010/0249604 | A1* | 9/2010 | Hastings ................. A61B 8/12 600/467 |
| 2012/0172871 | A1* | 7/2012 | Hastings ............... A61B 8/0891 606/41 |

OTHER PUBLICATIONS

Tokuda, Hiroyuki et al. "Physiochemical Properties and Structures of Room Temperature Ionic Liquids. 1. Variation of Anionic Species," J. Phys. Chem. B 2004, 108, 16593-16600. (Year: 2004).*

* cited by examiner

MECHANICALLY ROTATING INTRAVASCULAR ULTRASOUND PROBE

BACKGROUND

1. Technical Field

The present invention relates to the technical field of medical devices, and in particular to the technical field of intravascular ultrasound imaging devices used for interventional diagnosis and treatment.

2. Related Art

Intravascular ultrasound tomography (IVUS) is a novel diagnostic method combining a non-invasive ultrasonic diagnosis technology and a minimally invasive technology of interventional catheterization. As IVUS may accurately present a complex 3D anatomical structure of a blood vessel wall in real time, in addition to evaluating stenosis of lumen, it may further detect vulnerability of an atherosclerotic plaque and load of the plaque. Therefore, in the percutaneous coronary intervention treatment, IVUS has gradually replaced coronary angiography (CAG) that is originally deemed as a "gold standard" for diagnosis and treatment of a coronary heart disease, and becomes a novel diagnostic method widely applied clinically. The operation principle thereof is that, a small-sized ultrasonic transducer is installed on top of a flexible catheter about 140 cm long and about 1 mm thick, and the IVUS catheter is sent to a remote side of a target lesion location through a guide wire; during a process of pulling back the catheter (at a pullback rate of 0.5 mm/s), the ultrasonic transducer conducts 360° scanning around a blood vessel within a cavity of the blood vessel, and meanwhile, sends and receives high-frequency ultrasonic signals within the blood vessel, to implement cross-sectional imaging for each layer of the blood vessel wall, thereby assisting clinical doctors to give diagnosis for a coronary artery lesion. As a result, an intravascular ultrasound instrument includes three main components: 1) a catheter equipped with a micro ultrasonic transducer; 2) a pullback apparatus; and (3) a computerized ultrasound device with image rebuilding software and hardware. Undoubtedly, the catheter (i.e. ultrasound probe) equipped with the micro ultrasonic transducer directly operating within a narrow coronary artery is the core component that has the highest technical intensity in the entire intravascular ultrasound machine. The performance thereof directly affects quality of images and a signal-to-noise ratio, and also decides functions of system equipment and safety of use.

A commercialized intravascular ultrasound (IVUS) probe, according to structure thereof, may be roughly classified into 2 types: a mechanically rotating probe and an electronically scanned array probe. The electronically scanned array probe includes multiple (64 at most so far) array elements which are arranged in a ring shape on top of the catheter, to obtain a 360-degree cross-sectional image through sequential excitations by an electronic switch. The advantages thereof include that, neither a rotating part nor a conducting wire for connecting a single crystal is used; the guide wire passes through a central cavity thereof and easily passes through a target lesion; and it is not required to inject any liquid during use. However, there are disadvantages such as a lower image resolution and a 1-2 mm2 ultrasonic dead band easily occurring around the catheter. Although using more array elements may improve the imaging resolution, in the meantime, it will increase the volume of the probe, thus severely affecting application thereof as the intravascular probe. The mechanically rotating probe, may be further classified into 2 types, including a rotary reflector type probe (i.e. the transducer does not move but the reflector rotates) and a rotary transducer type probe, both of which are rotated (at a rate of 1,900 rpm) by a flexible driving rotary shaft within the catheter to obtain a 360-degree 2D cross-sectional image. Within a catheter of a single mechanical sector probe, gap between the transducer and a catheter sheath needs to be filled with a physiological saline solution, to achieve the best acoustic coupling. The type of mechanical sector probe, compared with the electronically scanned array probe, is advantageous in a higher imaging resolution, but the greatest disadvantage thereof is, when the catheter passes through a lesion with high-grade stenosis or a blood vessel section being curved, a friction may occur between a main shaft of the probe which is conducting rotary scanning and an inner cavity of the catheter to a great extent, thus obstructing free rotation of the catheter and causing rotation distortion to the image.

In addition, existing commercialized IVUS catheters may only help the doctors see an image of the blood vessel wall on a side of the ultrasound catheter, but fail to present an image of the blood vessel in front end thereof, such that their use is much restricted in Chronic Total Occlusion (CTO) lesions. As the most difficultly conquered problem in coronary arterial and peripheral arterial intervention treatment, CTO has a very high proportion among peripheral arterial diseases. A successful technology on blood vessel patency is the highest point of the intravascular interventional technique and CTO lesions have always constantly inspired wish of numerous clinical doctors to conquer them. The difficult problem of CTO in the medical field urgently demands research and development of forward-looking IVUS (FL-IVUS). It may be predicted that, a forward-looking IVUS catheter integrated with a radiofrequency ablation electrode may achieve visual stepwise ablation of a plaque within a partly or completely occluded blood vessel, and will provide a bright lamp for doctors performing an interventional operation, to give them the most "accurate" thoughts and therapies. Therefore, it has very broad application potential and great research significance.

SUMMARY

In view of disadvantages in existing intravascular ultrasound probes in the prior art, an objective of the present invention is to provide a forward-looking mechanically rotating intravascular ultrasound probe which has a small volume, a high image resolution, and good imaging stability.

In order to achieve the above objective, the present invention provides a mechanically rotating intravascular ultrasound probe, including a catheter, an ultrasonic transducer disposed at a front end of a cavity of the catheter and a driving apparatus that drives the ultrasonic transducer to rotate mechanically, where:

the driving apparatus is a micro motor disposed in the cavity of the catheter, the micro motor comprising a rotor and a stator, and the ultrasonic transducer is fixedly installed on top of the rotor and driven to rotate by the rotor;

the ultrasonic transducer is electrically connected to the rotor, and the rotor is also electrically connected to the stator, and electrical connections among the ultrasonic transducer, the rotor and the stator form a first channel of a signal transmission system;

the catheter is a magnetic metal tube, and the front end of the catheter is enclosed by an acoustic window which has a spherical tip, and allows ultrasonic waves of the ultrasonic transducer to pass through; and the acoustic window is filled with an ionic liquid having a function of an ultrasonic coupling agent, and an electrical connection between the ionic liquid and the catheter forms a second channel of the signal transmission system.

Furthermore, the rotor is a cylinder structure having a bevel on top thereof; the ultrasonic transducer is fixedly installed on the bevel and electrically connected to the rotor; the cylinder has a spherical recess at a bottom center thereof; the stator has a spherical protrusion that matches the spherical recess; the rotor is installed on the stator and makes the spherical protrusion a fulcrum of spinning; the rotor is electrically connected to the stator through the spherical protrusion; and exterior of the micro motor is treated to achieve insulation.

Furthermore, a diameter of the catheter is 1.5-2 mm.

Furthermore, the ionic liquid having the function of the ultrasonic coupling agent is preferably 1-ethyl-3-methylimidazolium dicyanamide, 1-ethyl-3-methylimidazolium bis(trifluoromethylsulfonyl)imide or 1-butyl-3-methylimidazolium tetrafluoroborate.

Furthermore, the ultrasonic transducer is connected to the rotor in a manner that, an emitting surface of the ultrasonic waves of the ultrasonic transducer and a rotation axis of the rotor form an angle of 0-90 degrees.

Furthermore, the intravascular ultrasound probe is further provided with a rotational speed sensor for measuring a rotational position and a rotational speed of the rotor in real time.

Furthermore, exterior of the ultrasonic transducer is also provided with a metal shield at a position other than a front emitting surface of the ultrasonic waves Furthermore, an exterior wall of the catheter is coated with a biologically compatible material.

Beneficial Effects:

Compared with the prior art, in the mechanically rotating intravascular ultrasound probe provided by the present invention, a narrow-neck micro motor is designed to be located in the catheter, which may achieve an outside diameter of the catheter between 1.5 mm and 2 mm, further reduce the volume of the probe, and solve the problem of rotation distortion of an image when the catheter passes through a lesion with high-grade stenosis or a curved blood vessel section. Additionally, by adjusting an angle of the ultrasonic transducer, the present invention achieves forward scanning imaging and side scanning imaging for a blood vessel wall. The design of the present invention is ingenious in that the ionic liquid is used as an electrical liquid brush to achieve electrical connection of the ultrasonic transducer during rotation. As the ionic liquid has a characteristic of acoustic impedance close to that of a biological tissue of a human body, it not only acts as the acoustic coupling agent, but also achieves a function of electrical conduction, thus enabling a top electrode of the ultrasonic transducer during rotation to be effectively grounded, and obtaining an electrical shielding effect. The rotor of the ultrasound probe drives the high-resolution high-frequency ultrasonic transducer to implement forward-looking conical scanning imaging for the blood vessel wall, and also utilizes the rotational speed sensor to measure the rotational position and the rotational speed of the rotor in real time, thus, in combination with a closed-loop control system, achieving accurate control over the rotational speed of the rotor as well as scanning synchronization with an imaging system.

1: catheter; 2: acoustic window; 3: micro motor; 31: rotor; 311: bevel; 312: spherical recess; 32: stator; 321: spherical protrusion; 4: high-frequency ultrasonic transducer; 5: metal shield; 6: ionic liquid.

DETAILED DESCRIPTION

The present invention will be further illustrated in detail below with reference to the accompanying drawings and specific embodiments. The following embodiments are only described for explaining the present invention, but the present invention is not limited to the following embodiments.

Figure 1:
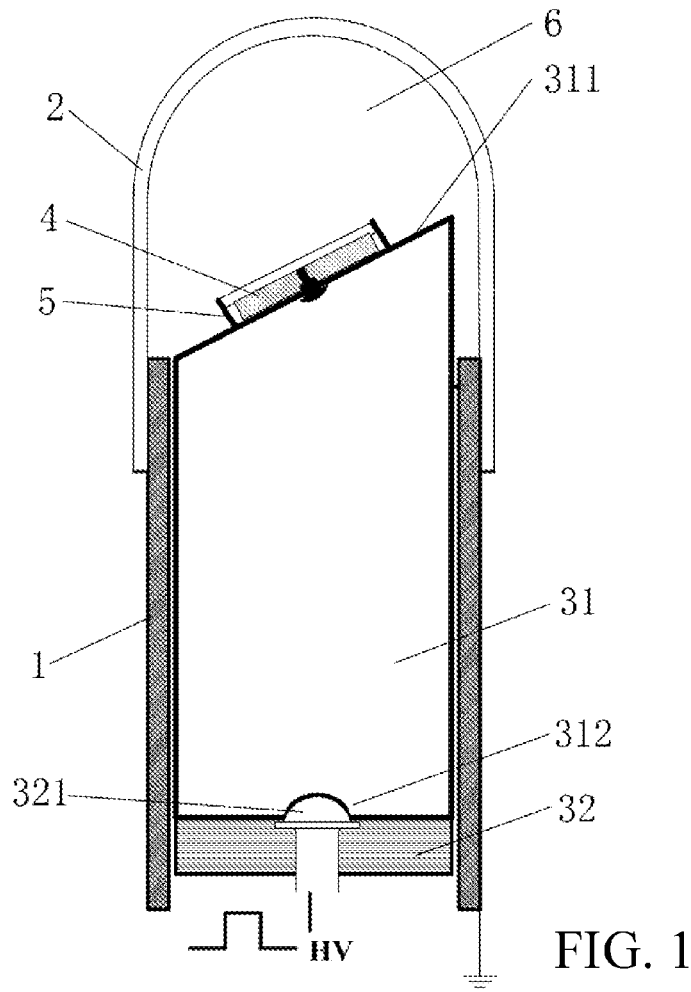
FIG. 1 is a structural diagram of an ultrasound probe according to one embodiment of the present invention.

FIG. 1 is a structural diagram of a mechanically rotating intravascular ultrasound probe according to one embodiment of the present invention. In this embodiment, the intravascular ultrasound probe comprises a catheter 1, an acoustic window 2, a micro motor 3 and a high-frequency ultrasonic transducer 4, where the catheter 1 is a magnetic metal tube with a diameter between 1.5 mm and 2 mm, and an exterior wall thereof is coated with a biologically compatible material; the acoustic window 2, which has a spherical tip, and allows ultrasonic waves to pass through, is installed in an front end of the catheter 1 to enclose the front end of the catheter 1; the micro motor 3 is installed in a cavity of the catheter 1 and the surface thereof is treated to achieve insulation, and the micro motor 3 is composed of a rotor 31 and a stator 32, where the rotor 31 is a cylinder structure having a bevel 311 on top thereof and a spherical recess 312 at a bottom center thereof, the stator 32 has a spherical protrusion 321 that matches the spherical recess 312, the rotor 31 is disposed above the stator 32, the spherical recess 312 and the spherical protrusion 321 are engaged closely by a prestressing force, the rotor 31 spins around the spherical protrusion 321 as a fulcrum, and the rotor 31 is electrically connected to the stator 32 through the spherical protrusion 321; the high-frequency ultrasonic transducer 4 is fixedly disposed on the bevel 311 and electrically connected to the rotor 31, and exterior thereof is provided with a metal shield 5 at a position other than an front emitting surface of the ultrasonic waves; a cavity enclosed by the acoustic window 2 and the catheter 1 is filled with an ionic liquid 6, which has a function of an ultrasonic coupling agent and may be selected from 1-ethyl-3-methylimidazolium dicyanamide, 1-ethyl-3-methylimidazolium bis(trifluoromethylsulfonyl)imide or 1-butyl-3-methylimidazolium tetrafluoroborate, a top electrode of the high-frequency ultrasonic transducer 4 is electrically connected to the ionic liquid 6, and the intravascular ultrasound probe further includes a rotational speed sensor (not shown) used for measuring a rotational position and a rotational speed of the rotor 31 in real time.

Figure 2:
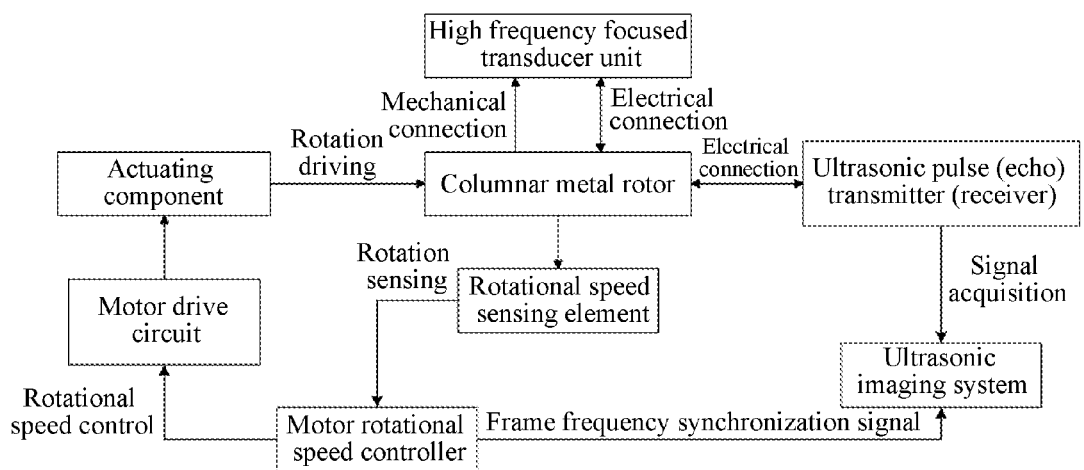
FIG. 2 is a block diagram illustrating the operating principle of the ultrasound probe in FIG. 1.

The ionic liquid in the intravascular ultrasound probe not only acts as the ultrasonic coupling agent, but also utilizes a characteristic of electrical conduction thereof to achieve effective grounding of the top electrode of the high-frequency ultrasonic transducer and electrical shielding of the probe by properly arranging electrodes. The surface of the micro motor with a special shape design is treated to achieve insulation. The spherical protrusion not only acts as the fulcrum of spinning for the rotor of the micro motor, but also as an input electrode for electrical pulse signals, connecting high-voltage electrical pulses to a signal electrode of the high-frequency ultrasonic transducer through conduction of the rotor of the micro motor. Due to instability of an outside driving force plus a friction force of an interior wall of the catheter, it may often result in an unstable rotational speed of the probe. The present invention establishes a closed-loop control system, and introduces a micro rotational speed sensor embedded below the micro rotor for measuring the rotational position and the rotational speed of the rotor in real time. In combination with the closed-loop control system, the present invention achieves accurate control over the rotational speed of the rotor, as well as synchronization with an imaging system. A block diagram illustrating the operating principle of the ultrasound probe is as shown in FIG. 2.

What is claimed is:

1. A mechanically rotating intravascular ultrasound probe, comprising a catheter, an ultrasonic transducer disposed at a front end of a cavity of the catheter and a driving apparatus that drives the ultrasonic transducer to rotate mechanically, wherein:
   the driving apparatus is a micro motor disposed in the cavity of the catheter, the micro motor comprising a rotor and a stator, and the ultrasonic transducer is fixedly installed on top of the rotor and is driven to rotate by the rotor;
   the ultrasonic transducer is electrically connected to the rotor, and the rotor is also electrically connected to the stator, and electrical connections among the ultrasonic transducer, the rotor and the stator form a first electrical channel for transmitting electrical pulse signals generated by the ultrasonic transducer;
   the catheter is a magnetic metal tube, and the front end thereof is enclosed by an acoustic window which has a spherical tip, and allows ultrasonic waves of the ultrasonic transducer to pass through; and
   the acoustic window is filled with ionic liquid having ultrasonic coupling, a second electrical channel includes an electrode of the ultrasonic transducer, the ionic liquid and the catheter that is grounded, the second electrical channel is configured to ground the electrode of the ultrasonic transducer to obtain an electrical shielding effect for the transducer.

2. The mechanically rotating intravascular ultrasound probe according to claim 1, wherein the rotor is a cylinder structure having a bevel on top thereof; the ultrasonic transducer is fixedly installed on the bevel and electrically connected to the rotor; the cylinder structure has a spherical recess at a bottom center thereof; the stator has a spherical protrusion that matches the spherical recess; the rotor is installed on the stator and makes the spherical protrusion a fulcrum of spinning; the rotor is electrically connected to the stator through the spherical protrusion; and exterior of the micro motor is treated to achieve insulation.

3. The mechanically rotating intravascular ultrasound probe according to claim 1, wherein a diameter of the catheter is 1.5-2 mm.

4. The mechanically rotating intravascular ultrasound probe according to claim 1, wherein the ionic liquid is 1-ethyl-3-methylimidazolium dicyanamide, 1-ethyl-3-methylimidazolium bis(trifluoromethyl sulfonyl)imide or 1-butyl-3-methylimidazolium tetrafluoroborate.

5. The mechanically rotating intravascular ultrasound probe according to claim 1, wherein the ultrasonic transducer is connected to the rotor in a manner that an emitting surface of the ultrasonic waves of the ultrasonic transducer and a rotation axis of the rotor form an angle in a range from 0 degree to 90 degree.

6. The mechanically rotating intravascular ultrasound probe according to claim 1, wherein the intravascular ultrasound probe is further provided with a rotational speed sensor for measuring a rotational position and a rotational speed of the rotor in real time.

7. The mechanically rotating intravascular ultrasound probe according to claim 1, wherein exterior of the ultrasonic transducer is also provided with a metal shield at a position other than a front emitting surface of the ultrasonic waves.

8. The mechanically rotating intravascular ultrasound probe according to claim 1, wherein an exterior wall of the catheter is coated with a biologically compatible material.

9. The mechanically rotating intravascular ultrasound probe according to claim 1, wherein the ultrasonic transducer is fixedly installed directly on top of the rotor and is driven to rotate by the rotor.

10. The mechanically rotating intravascular ultrasound probe according to claim 1, wherein the ionic liquid is 1-ethyl-3-methylimidazolium bis(trifluoromethylsulfonyl)imide or 1-butyl-3-methylimidazolium tetrafluoroborate.

11. The mechanically rotating intravascular ultrasound probe according to claim 6, further comprising a closed-loop control system for achieving an accurate control of rotational speed of the rotor and for scanning synchronization with the ultrasonic transducer.

12. The mechanically rotating intravascular ultrasound probe according to claim 6, the rotational speed sensor is embedded below the rotor.

* * * * *